United States Patent [19]

Kubofcik

[11] Patent Number: 4,907,717

[45] Date of Patent: Mar. 13, 1990

[54] LOW-LEVEL RADIATION WASTE MANAGEMENT SYSTEM

[76] Inventor: Kenneth W. Kubofcik, 6 Quail Ct., Shelton, Conn. 06484

[21] Appl. No.: 157,384

[22] Filed: Feb. 18, 1988

[51] Int. Cl.$^4$ ............................................. B65D 90/04
[52] U.S. Cl. .................................. 220/404; 250/506.1; 250/519.1; 252/633; 383/80; 383/113
[58] Field of Search .............................. 220/403, 404; 250/506.1, 507.1, 519.1; 252/633; 383/113, 78, 80

[56] References Cited

U.S. PATENT DOCUMENTS

| | | | |
|---|---|---|---|
| 3,039,001 | 6/1962 | Park et al. | 250/519.1 |
| 3,536,920 | 10/1970 | Sedlak et al. | 250/519.1 |
| 3,845,316 | 10/1974 | Tureck | 250/519.1 |
| 4,058,479 | 11/1977 | White et al. | 250/506.1 X |
| 4,090,087 | 5/1978 | Weissenfluh | 250/519.1 |
| 4,357,541 | 11/1982 | Ernst | 250/507.1 |
| 4,409,029 | 10/1983 | Larker et al. | 252/633 X |
| 4,599,518 | 7/1986 | Schmidt et al. | 250/507.1 |
| 4,625,122 | 11/1986 | Botzem et al. | 250/506.1 |
| 4,633,091 | 12/1986 | Kurasch et al. | 252/633 X |
| 4,642,204 | 2/1987 | Burstrom et al. | 252/633 |

FOREIGN PATENT DOCUMENTS

| | | | |
|---|---|---|---|
| 2439460 | 6/1980 | France | 250/519.1 |
| 0025798 | 3/1978 | Japan | 250/519.1 |

Primary Examiner—Stephen Marcus
Assistant Examiner—Nova Stucker
Attorney, Agent, or Firm—Parmelee, Bollinger & Bramblett

[57] ABSTRACT

A low-level radiation waste management system collects low-level radiation wastes in hospitals, etc. The system includes a cylindrical fiberboard receptacle and a receptacle liner which is deployed in the barrel and has its upper marginal edge everted over the side of the barrel. A cover including a depending skirt is removably positioned covering the top of the barrel the skirt surrounding the upper portion of the barrel and the everted liner. The receptacle liner and cover are fabricated of radiation shielding material, e.g. panels vinyl encapsulated lead with vinyl outer sheeting dielectrically welded together. After wastes have been collected, the cover is placed in the receptacle liner over the wastes, and the everted portion of the receptacle liner is pulled up and, gathered and tied. This portion of the receptacle liner is uncontaminated. The receptacle liner with the cover and wastes inside may be transported to a disposal site and buried.

21 Claims, 1 Drawing Sheet

LOW-LEVEL RADIATION WASTE MANAGEMENT SYSTEM

FIELD OF INVENTION

This invention relates to the collection, containment and disposal of low-level radiation waste materials.

BACKGROUND OF INVENTION

Hospitals, scientific laboratories and other similar facilities require the capability of collecting, containing and disposing of low-level radiation waste materials. In a hospital, for instance, the materials may comprise bandages, dressings, patient drapes, tubing or equipment, etc. which become contaminated during radiation treatments.

Such low-level radiation wastes are presently managed by placing a lead-lined metal container in the treatment area. The lead-lined metal container is open-topped and includes a lead-lined lid member providing closure; the system is basically a lead-lined barrel with a lid. Upon being filled, the entire barrel and lid structure must be removed as a unit, including wastes, and a new one placed at the collection site. The rigid metal drum and its lead lining comprise a container which is heavy and bulky and which cannot be moved by hand. Accordingly, it is necessary to utilize machinery such as cart or small forklift to remove a filled container and place a new container. This adds considerable expense, complexity and inconvenience of collection low-level radiation waste.

Similar considerations carry over to disposal of the low-level radiation wastes collected in metal/lead drums. Generally, the drums are trucked to a storage site and are buried. The aforementioned problems of handling a heavy, bulky drum continue in the disposal phase and, further, the final result is the disposal of a relatively expensive drum structure together with the low-level radiation waste.

SUMMARY OF INVENTION

It is a principal object of the invention herein to provide an improved way of collecting, containing and disposing of low-level radiation waste materials.

It is an additional object of the invention herein to provide an efficient, low-cost way of collecting, containing and disposing of low-level radiation waste material.

It is a further object of the invention herein to provide a low-level radiation waste management system for collecting, containing, transporting and disposing of the radioactive waste materials.

It is yet another object of the invention to provide a low-level radiation waste management system which is inexpensive to manufacture and causes minimum intrusion upon and disruption of activities at the collection/containment site.

A low-level radiation waste management system according to the invention herein comprises a container set including a liner having a closed end and an open end, and being adapted for deployment in a rigid open-topped receptacle for receiving low-level radiation waste. The receptacle liner includes a tie-receiving closure portion adjacent the open end, said closure portion being evertable to lie on the exterior of the open-topped receptacle. A cover is adapted to fit over the open-topped receptacle and the receptacle liner therein, the cover including a skirt portion to assure overlapping relationship.

The receptacle liner and cover are fabricated of a material, preferably a vinyl-encapsulated lead material, which absorbs radiation and prevents the passage of radiation from within the receptacle.

When it is desired to remove the accumulated low-level radiation waste, the cover may be dropped into the receptacle liner, continuing to provide a shield from the waste. Although the underside of the cover and the interior of the receptacle liner become contaminated by radiation emanating from the collected low-level radiation waste, the everted liner portion remains uncontaminated and may be uneverted, gathered and tied to close the receptacle liner. It will be appreciated that the portion of the receptacle liner extending above the tie is uncontaminated and presents no health hazard. The tied receptacle liner provides a relatively lightweight and easily handled package for transport to a disposal site, where it may be buried. The receptacle liner may be used with a fiberboard barrel or other receptacle, which may be maintained at the collection site and reused with subsequently installed receptacle liners and covers.

In a preferred embodiment, the receptacle liner and cover are fabricated of a three-layer material including two layers of a vinyl film sandwiching the vinyl-encapsulated lead sheet, and the seams are dielectrically welded to provide an air-tight and water-tight seal.

Other and more specific features and objects of the invention herein will in part be apparent to those skilled in the art and will in part also appear from the following description of the preferred embodiment and the claims taken together with the drawings.

DRAWINGS

The same reference numerals refer to the same elements throughout the various Figures.

DESCRIPTION OF PREFERRED EMBODIMENT

A low-level radiation waste management system according to the invention herein generally comprises a receptacle having an open-top and a container set including a receptacle liner received in the receptacle and a cover removably received over the open top of the receptacle.

Figure 1:
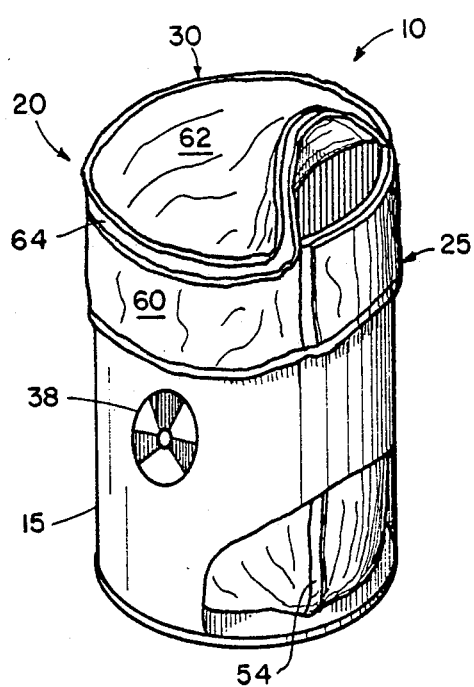
FIG. 1 is a perspective view of a low-level radiation waste management system according to the invention herein.
Figure 2:
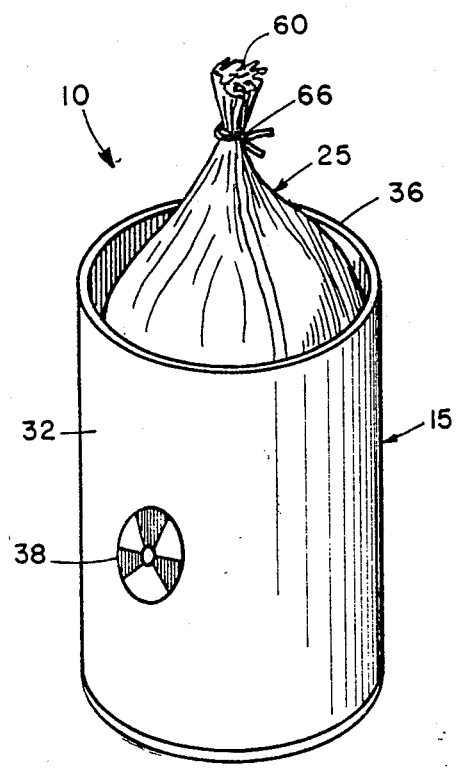
FIG. 2 is a perspective view of the low-level radiation waste management system of FIG. 1, shown containing collected waste and closed for transport and disposal.
Figure 3:
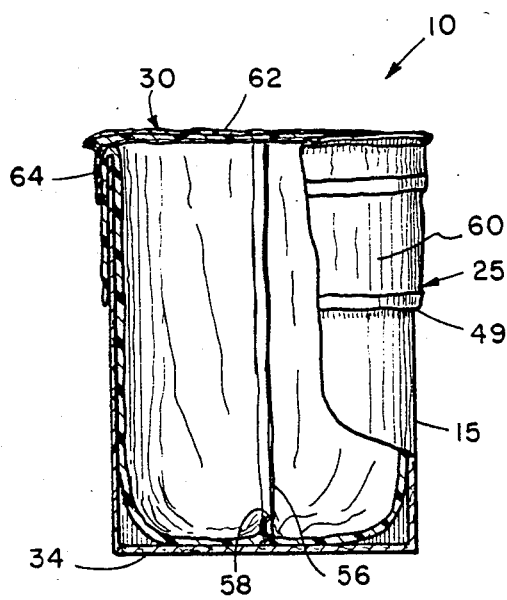
FIG. 3 is a sectional view, partially cut away, of the low-level radiation waste management system of FIG. 1.
Figure 4:
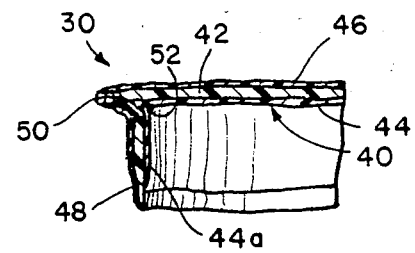
FIG. 4 is an enlarged fragmentary sectional view of a seam portion of the low-level radiation waste management system of FIG. 1.

With reference to FIGS. 1-3, a preferred embodiment 10 of a low-level radiation waste management system according to the invention herein is illustrated. FIG. 4 shows details of its structure. The low-level radiation waste management system 10 generally comprises a receptacle 15 and a container set 20, the container set 20 including a receptacle liner 25 and a cover 30.

The receptacle 15, which is perhaps best seen in FIG. 2, is an open-topped barrel including a cylindrical sidewall 32 and a bottom 34 (FIG. 3). The upper edge 36 of the cylindrical sidewall 32 defines the open top of the receptacle 15. As more fully discussed below, the receptacle 15 supports the container set 20 in operative position, but the receptacle 15 itself does not need to provide any radiation shielding function. Accordingly, the receptacle 15 is fabricated of sturdy fiberboard, although fiberglass or metal containers are suitable as well.

The receptacle 15 is placed at the desired location for collecting low-level radiation wastes, and does not have to be moved from that location in order to dispose of the waste. The receptacle 15 is also preferably marked with the radiation warning symbol, as indicated at 38.

The container set 20 includes the receptacle liner 25 and cover 30. The material from which the container set 20 is fabricated is best seen in FIG. 4, which is an enlarged sectional view of a portion of the cover 30. The material, which is given the general number 40 in FIG. 4, comprises a central layer 42 of vinyl-encapsulated lead which is an effective block of the radiation emanating from low-level radiation wastes. The material 40 further comprises first and second vinyl (PVC) sheets 44 and 46 flanking the central vinyl-encapsulated lead sheet 42. The vinyl sheets 44 and 46 separate the central layer from user contact, thereby preventing the user from contacting and absorbing lead from the central layer.

The vinyl sheets 44, 46 and also contribute to the strength, liquid, integrity, and seam sealing properties of the material 40. A seam 50 between two adjacent panels of the material 40 is best illustrated in FIG. 4. The seam 50 is preferably formed by dielectric welding, which fuses the six total layers of the two panels together. Of particular importance from a sealing standpoint is that the inside layers 44 and 44a of the adjacent panels fuse and form a liquid tight seal, almost akin to a bead, at 52. Overlapping seams are also used as appropriate, and edges are fused as at 48, or may be stitched (not shown). It will be appreciated that the vinyl sheets 44, 46 may be bonded or coated to the outer surfaces of the vinyl-encapsulated lead 42, or may be merely a coating thereon.

The receptacle liner 25 is fabricated of two panels of the material 40, having side seam 54 best seen in FIG. 1, and side seam 56 and bottom seam 58, the latter two seams being best seen in FIG. 3. The side seams 54, 46 are preferably overlapped, dielectrically welded seams, and the bottom seam 58 is inturned and dielectrically welded. The top of the receptacle liner 25 is left open and the upper edge 49 is fused or stitched to join the three layers of material.

The receptacle liner 25 is inserted into the receptacle 15 and is of sufficient length to provide an upper tie-receiving closure portion 60 which is everted to lie on the exterior of the receptacle 15 during the on-site collection and containment functions, per FIGS. 1 and 3. The cover 30 comprises a top panel 62 sized and shaped to fit over the open top of the receptacle 15, including the everted tie-receiving closure portion 60 thereof, and a depending skirt 64 extending along the everted tie-receiving closure portion 60 on the exterior of receptacle 15. The overlap of the skirt 64 over the receptacle 15 ensures there is no direct path for radiation to escape the low-level radiation waste management system when the cover 30 is in its closed position.

The low-level radiation waste management system 10 is utilized by first placing the receptacle liner 25 in the receptacle 15, with the tie-receiving closure portion 60 everted to lie along the exterior of the receptacle. The cover is fitted over the top of the receptacle and receptacle liner. As illustrated in FIG. 1, the cover may be partially folded back or even completely opened to deposit low-level radiation wastes in the receptacle liner. Of course, the cover 30 is promptly returned to its fully closed position after the waste has been deposited. The receptacle liner 25 and cover 30 prevent the escape of radiation during storage of waste materials at the collection site. Although the interior of the receptacle liner 25 received within the receptacle and the underside of the cover 30 become contaminated by the low-level radiation waste, the everted tie-receiving closure portion 60 remains uncontaminated during this collection and containment function.

When the receptacle has been filled, or at a scheduled collection interval, the following procedure is utilized to confine and transport the low-level radiation waste. The cover is pressed into the receptacle liner, covering the wastes collected therein. Next, the everted tie-receiving closure portion 60 is pulled upwardly and gathered as shown in FIG. 2, and a tie 66 is placed about the gathered portion. It will be appreciated that some of the tie-receiving closure portion 60 is exposed above the tie 66, but that the exposed portion of the tie-receiving closure portion 60 has remained uncontaminated and does not in and of itself present any hazard. Although the gathering at the tie is generally sufficient to prevent the escape of radiation, having the cover placed over the waste below the tie is additional protection against any possible escape paths.

The tied receptacle liner, including the cover and wastes contained therein, is lifted from the receptacle 15 and may be carried or placed on a lightweight cart to remove it from the collection site. The receptacle liner may be transported to a collection site and may be buried there with the low-level radiation waste still contained therein. Of course, the receptacle liner is flexible and permits the low-level radiation wastes to be compacted as they are buried, unlike a rigid barrel system.

At the collection site, a new container set 20 is installed in the receptacle 15, and additional low-level radiation wastes are collected and contained therein.

Accordingly, the low-level radiation waste management system described above admirably achieves the objects of the invention herein. It will be appreciated, however, that the low-level radiation waste management system described is a preferred embodiment and in and of itself does not represent the full scope of the invention herein. For instance, the receptacle need not be cylindrical, and the receptacle liner and cover may be shaped appropriately for use with any receptacle shape. The location of the seams and shape of the receptacle liner may also be varied, and a more snug fit within a cylindrical receptacle could be achieved by providing the receptacle liner with a circular bottom panel, albeit at increased fabrication cost. It will further be appreciated that any flexible radiation absorbing material may be used in fabricating a container set and that the thickness of the material is selected according to its ability to block radiation and the volume of wastes to be contained therein. These and other changes departures from the preferred embodiment described above may be made by those skilled in the art without departing from the spirit and scope of the invention, which is limited only by the following claims.

I claim:

1. A low-level radiation waste container set for use in conjunction with an open-topped receptacle, the container set comprising:
   A. a receptacle liner having a closed end and an open end, the receptacle liner sized for deployment as an inserted liner in an open-topped receptacle for collecting low-level radiation waste material within the receptacle liner within the open-topped receptacle;
   B. a cover sized and shaped to fit over the open top of the open-topped receptacle and the receptacle liner therein with the cover is in a closed position, the cover having a depending skirt which, when the cover is in the closed position, extends downwardly to overlap the open-topped receptacle adjacent the open top thereof and a portion of the receptacle liner received therein; and
   C. the receptacle liner and cover being fabricated of flexible radiation shielding material, whereby the cover may be partially opened to insert low-level radiation waste material and the cover may be inserted into the receptacle liner for disposal.

2. A low-level radiation waste container set as defined in claim 1 wherein the receptacle liner includes a tie-receiving closure portion adjacent the open end thereof, said closure portion being evertable for deployment on the exterior of the open-topped receptacle where it remains uncontaminated during the collection of low-level radiation waste material, and the tie-receiving closure portion being unevertable and gatherable to receive a tie for sealing the receptacle liner preparatory to transport and disposal.

3. A low-level radiation waste container set as defined in claim 2 wherein the flexible radiation shielding material includes a layer of vinyl-encapsulated lead.

4. A low-level radiation waste container set as defined in claim 3 wherein the radiation shielding material further includes two vinyl sheets being deployed on respective sides of the layer of vinyl-encapsulated lead.

5. A low-level radiation waste container set as defined in claim 4 wherein the receptacle liner and cover are each made of panels of the flexible radiation shielding material joined together by dielectric welds.

6. A low-level radiation waste container set as defined in claim 5 wherein the receptacle liner is fabricated of two panels of the flexible radiation shielding material joined together by dielectrically welded seams on three sides thereof.

7. A low-level radiation waste container set as defined in claim 5 wherein the depending skirt is joined to the remaining cover portion by a dielectric weld.

8. A low-level radiation waste container set as defined in claim 4 wherein the radiation shielding material further includes dielectrically welded edges joining the two vinyl sheets with the layer of vinyl-encapsulated lead.

9. A low-level radiation waste container set as defined in claim 1 wherein the receptacle liner and cover are each made of panels of the flexible radiation shielding material joined together by dielectric welds.

10. A low-level radiation waste management system comprising:
    A. an open-topped rigid receptacle;
    B. a receptacle liner having a closed end and an open end, the receptacle liner sized for deployment as a liner in the open-topped receptacle for collecting low-level radiation waste material;
    C. the receptacle liner including a tie-receiving closure portion adjacent the open end thereof, said closure portion being evertable to lie on the exterior of the open-topped receptacle when the receptacle liner is deployed therein; and
    D. a cover sized and shaped to fit over the open top of the receptacle and the receptacle liner therein when the cover is in a closed position, the cover including a depending skirt which, when the cover is in its closed position, extends downward to overlap the upper marginal edge of the receptacle and at least a portion of the everted tie-receiving closure portion of the receptacle liner;
    E. the receptacle liner and cover being fabricated of flexible radiation shielding material.

11. A low-level radiation waste management system as defined in claim 10 wherein the receptacle is cylindrical.

12. A low-level radiation waste management system as defined in claim 11 wherein the receptacle is fiberboard.

13. A low-level radiation waste management system as defined in claim 10 wherein the flexible radiation shielding material includes a layer of vinyl-encapsulated lead.

14. A low-level radiation waste management system as defined in claim 13 wherein the radiation shielding material further includes two vinyl sheets being deployed on respective sides of the layer of vinyl-encapsulated lead.

15. A low-level radiation waste management system as defined in claim 14 wherein the receptacle liner and cover are each made of panels of the flexible radiation shielding material joined together by dielectric welds.

16. A low-level radiation waste management system as defined in claim 15 wherein the receptacle liner is fabricated of two panels of the flexible radiation shielding material joined together by dielectrically welded seams on three sides thereof.

17. A low-level radiation waste management system set as defined in claim 15 wherein the depending skirt is joined to the remaining cover portion by a dielectric weld.

18. A low-level radiation waste management system as defined in claim 14 wherein the radiation shielding material further includes dielectrically welded edge seams joining the two vinyl sheets with the layer of vinyl-encapsulated lead.

19. A low-level radiation waste container as defined in claim 10 wherein the receptacle liner and cover are each made of panels of the flexible radiation shielding material joined together by dielectric welds.

20. A low-level radiation waste container set comprising:
    A. a receptacle liner having a closed bottom and a sidewall joined therewith and extending to an upper, open end, the sidewall including a upper, tie-receiving closure portion everted adjacent the upper open end;
    B. a cover sized and shaped to fit over and cover the upper, open end of the receptacle liner, the cover having a peripheral depending skirt which, when the cover is in its closed position fitted over the open end of the receptacle liner, extends downwardly to overlap the everted tie-receiving closure portion of the receptacle liner; and
    C. the receptacle liner and cover being fabricated of flexible, radiation shielding material, wherein the cover may be partially opened to insert low-level radiation waste material, and wherein the cover may be inserted into the receptacle liner and the upper, tie-receiving portion may be un-everted, gathered and tied to enclose the low-level radiation waste material and cover for transportation to a disposal site.

21. A low-level radiation waste container set comprising:

A. a receptacle liner having a closed bottom and a sidewall joined therewith and extending to an upper open end, the receptacle liner adapted to be supported in an open-topped receptacle with the upper, open end of the receptacle adjacent the open top of the receptacle;

B. a cover sized and shaped to fit over and cover the upper, open end of the receptacle liner, the cover having a peripheral depending skirt which, when the cover is in its closed position fitted over the open end of the receptacle liner, extends downwardly to overlap the upper, open end of the receptacle; and C. the receptacle liner and cover being fabricated of flexible radiation shielding material, whereby the cover may be partially opened to insert low-level radiation waste material into the receptacle liner.

* * * * *